United States Patent [19]
Cohen et al.

[11] Patent Number: 6,162,201
[45] Date of Patent: Dec. 19, 2000

[54] INTERNAL URINARY CATHETER

[76] Inventors: Kenneth L. Cohen, 9 Bishop Dr., Woodbridge, Conn. 06525; Dennis Hanlon, 15 Horris Rd., East Haven, Conn. 06512

[21] Appl. No.: 09/088,166

[22] Filed: Jun. 1, 1998

Related U.S. Application Data

[63] Continuation-in-part of application No. PCT/US96/19154, Dec. 2, 1996, which is a continuation-in-part of application No. 08/566,356, Dec. 1, 1995, Pat. No. 5,785,694.

[51] Int. Cl.[7] .................................................. A61M 5/00
[52] U.S. Cl. ................. 604/250; 604/99.02; 604/101.01
[58] Field of Search ...................... 600/31, 30; 604/350, 604/323, 328, 30, 34, 247, 248, 250, 96.01, 97.01, 99.02, 99.03, 99.04, 101.01; 251/4–7; 606/192, 194

[56] References Cited

U.S. PATENT DOCUMENTS

| | | |
|---|---|---|
| Re. 33,219 | 5/1990 | Daniell et al. . |
| 1,880,948 | 6/1932 | Evennett . |
| 2,471,623 | 5/1949 | Hubbell . |
| 2,709,542 | 5/1955 | Eller et al. . |
| 3,812,841 | 5/1974 | Isaacson . |
| 4,148,319 | 4/1979 | Kasper et al. . |
| 4,211,233 | 7/1980 | Lin . |
| 4,350,161 | 9/1982 | Davis, Jr. . |
| 4,432,757 | 2/1984 | Davis, Jr. . |
| 4,579,554 | 4/1986 | Glassman . |
| 4,642,104 | 2/1987 | Sakamoto et al. . |
| 4,813,935 | 3/1989 | Haber et al. . |
| 4,932,938 | 6/1990 | Goldberg et al. . |
| 4,946,449 | 8/1990 | Davis, Jr. . |
| 5,004,454 | 4/1991 | Beyar et al. . |
| 5,030,199 | 7/1991 | Barwick et al. . |
| 5,041,092 | 8/1991 | Barwick . |
| 5,306,226 | 4/1994 | Salama . |
| 5,306,241 | 4/1994 | Samples . |
| 5,429,620 | 7/1995 | Davis . |
| 5,522,806 | 6/1996 | Schonbachler et al. . |

*Primary Examiner*—Wynn Wood Coggins
*Assistant Examiner*—Deborah Blyveis
*Attorney, Agent, or Firm*—Bachman & LaPointe, P.C.

[57] ABSTRACT

A urinary catheter includes a cannula having a urine passage, a urine inlet and a urine outlet; and a valve positioned in said urine passage between said inlet and said outlet and having a valve passage having at least a portion which is moveably positioned between a substantially blocked positioned and a flow position, and structure for moving said portion, said structure for moving being biased toward a blocking position wherein said portion is in said substantially blocked position and flow through said valve means is substantially blocked, and said structure for moving being moveable to a position at least partially moving said portion toward said flow position wherein flow through said valve means is allowed.

55 Claims, 7 Drawing Sheets

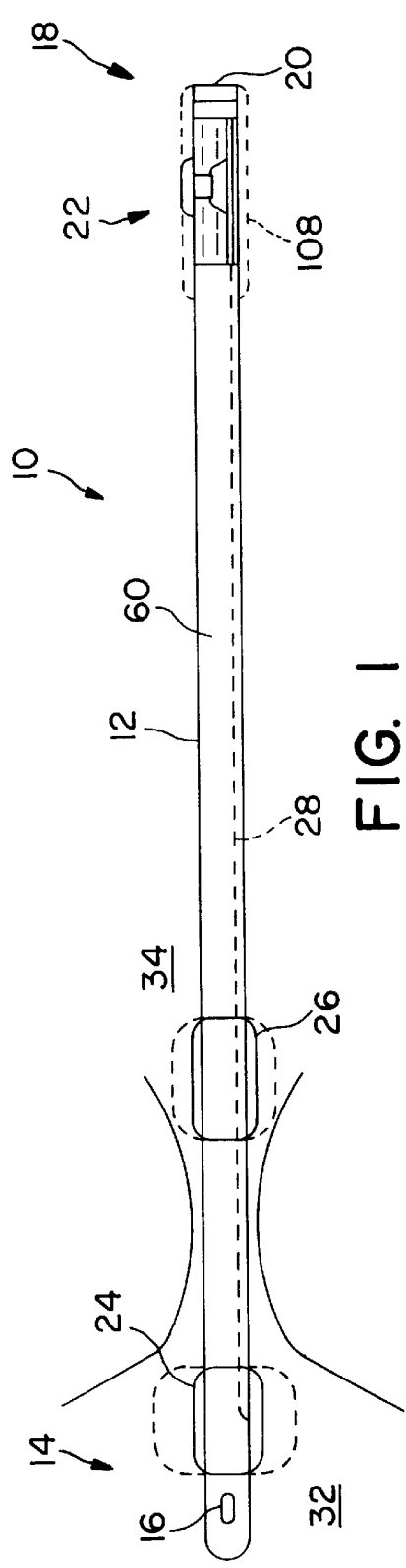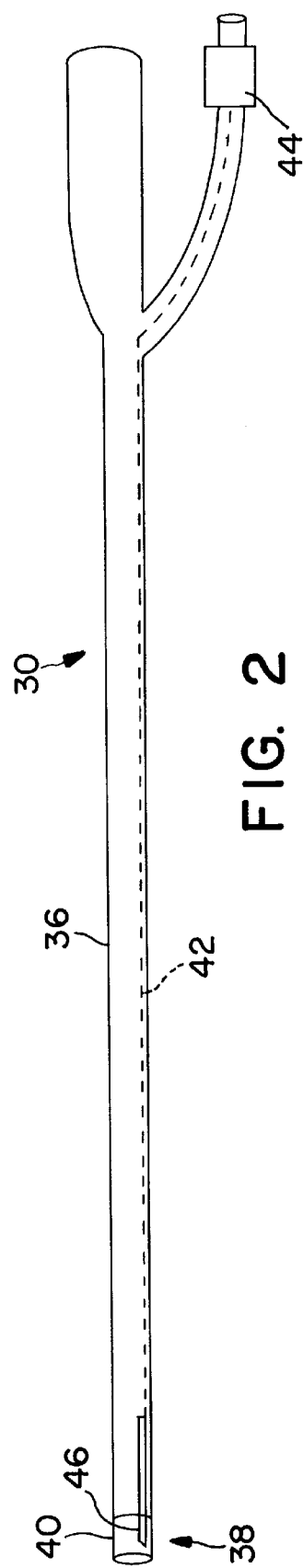

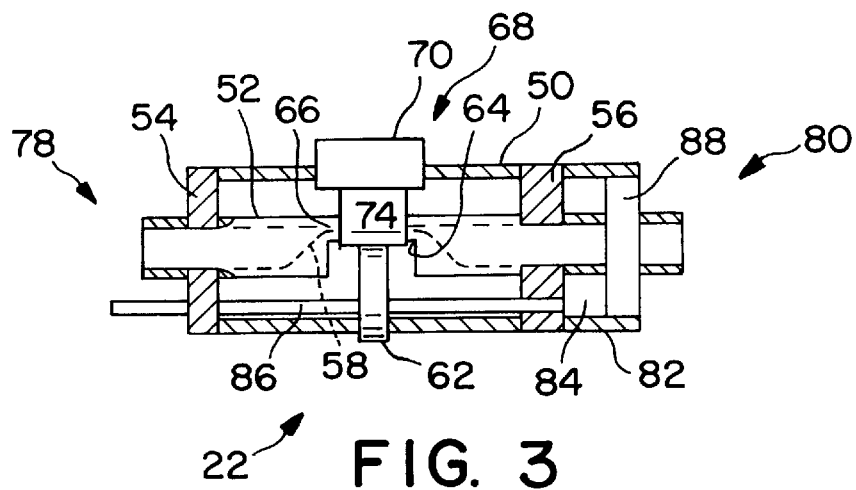
FIG. 3
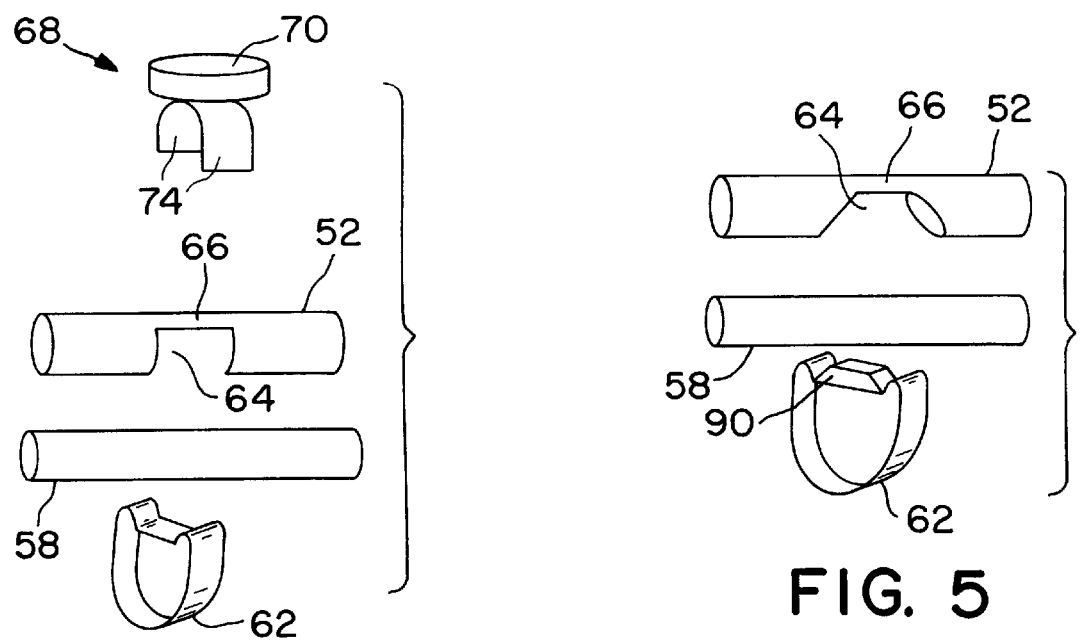
FIG. 4
FIG. 5
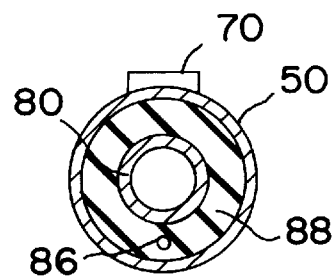
FIG. 6

INTERNAL URINARY CATHETER

This is a Continuation-in-Part of PCT Application No. PCT/US96/19154, filed Dec. 2, 1996 which is a Continuation-in-Part of U.S. patent application Ser. No. 08/566,356, filed Dec. 1, 1995, now U.S. Pat. No. 5,785,694.

BACKGROUND OF THE INVENTION

The invention relates to an internal urinary catheter, especially an internal urinary catheter for male patients having obstructive uropathy or urinary incontinence.

Catheterization of the bladder with flexible rubber tubes to relieve obstructed urine flow in male patients is a well established procedure. Chronic obstruction may be treated by intermittent (several times per day) straight catheterization or by placement of an indwelling catheter. Intermittent self-catheterization is an uncomfortable procedure that also incurs the risk of repeated urinary infections. Conventional indwelling catheters invariably become colonized with bacteria and also require an attached collecting bag. Urinary incontinence is extremely difficult to treat; artificial sphincters must be surgically implanted and are prone to many complications.

Numerous attempts have been made at developing internal urinary catheters. However, these devices include complicated valve mechanisms and the like, which lead to complications during use of same, particularly with respect to complicated valve components which are exposed to urine during use and which increase the likelihood of bacteria colonization. The need remains for an internal urinary catheter having a simple but reliable valve structure.

It is therefore the primary object of the present invention to provide an internal urinary catheter having a reliable and easily operable valve which does not have complicated valve components exposed to urine during use.

It is a further object of the present invention to provide a urinary catheter having a valve which is easily operated by a patient.

It is a still further object of the present invention to provide a urinary catheter which can be reliably positioned with respect to the bladder and urethra.

It is another object of the invention to provide an internal urinary catheter having an insertion member for activating catheter retention members when the catheter is within the urethra.

It is still another object of the present invention to provide a method for catheterization and use of a catheter in accordance with the present invention.

Other objects and advantages of the present invention will appear hereinbelow.

SUMMARY OF THE INVENTION

In accordance with the present invention, the foregoing objects and advantages are readily attained.

According to the invention, a urinary catheter is provided which comprises a cannula having a urine passage, a urine inlet and a urine outlet; and valve means positioned in said urine passage between said inlet and said outlet and comprising a valve passage having at least a portion which is moveably positioned between a substantially blocked position and a flow position, and means for moving said portion, said means for moving being biased toward a blocking position wherein said portion tube is in said substantially, blocked position and flow through said valve means is substantially blocked, and said means for moving being positionable to a released position at least partially moving said portion toward said flow position wherein flow through said valve means is allowed.

In further accordance with the invention, a valve for an internal urinary catheter is provided which comprises a passage for urine flow; a valve passage positioned along said passage and having at least a portion which is moveably positioned between a substantially blocked position and a flow position; and means for moving said portion, said means for moving being biased toward a blocking position wherein said portion is in said substantially blocked position and flow through said valve passage is substantially blocked, and said means for moving being positionable to a released position at least partially moving said portion toward said flow position wherein flow through said valve passage is allowed.

In still further accordance with present invention, a method for controlling urine flow in the urethra, comprising the steps of providing a cannula having a urine passage, an inlet end having a urine inlet, an outlet end having a urine outlet and valve means positioned along said urine passage for limiting flow from said urine inlet to said urine outlet, said valve means comprising a valve passage having at least a portion which is moveably positioned between a substantially blocked position and a flow position, and means for moving said portion, said means for moving being biased toward a blocking position wherein said portion is in said substantially blocked position and flow through said valve means is substantially blocked, and said means for moving being positionable to a released position at least partially moving said portion toward said flow position wherein flow through said valve means is allowed; positioning said cannula in the urethra with said urine inlet in the bladder; and moving said means for moving to said released position so as to allow flow of urine from the bladder through said urine passage and said valve passage to said urine outlet.

Still further according to the invention, a method is provided for positioning an internal urinary catheter within the urethra, comprising the steps of providing a catheter comprising a urine passage, a urine inlet, a urine outlet, valve means for controlling urine flow from said urine inlet to said urine outlet, a bladder retention balloon positioned proximate to said urine inlet, a urethra retention balloon spaced toward said outlet end from said bladder retention balloon, and a balloon fluid passage communicating with said bladder retention balloon and said urethra retention balloon;

positioning said catheter in the urethra with said urine inlet and said bladder retention balloon in the bladder adjacent the neck and orifice of the bladder, and with said urethra retention balloon in the urethra adjacent the neck and orifice of the bladder; and inflating said bladder retention balloon and said urethra retention balloon whereby said bladder retention balloon retains said urine inlet within the bladder and said urethra retention balloon retains said catheter within the urethra against back migration into the bladder.

BRIEF DESCRIPTION OF THE DRAWINGS

A detailed description of preferred embodiments of the invention follows, with reference to the attached drawings, wherein:

FIG. 1 is a side view of an internal urinary catheter according to the invention;

FIG. 2 is a side view of an insertion member for an internal urinary catheter according to the invention;

FIG. 3 is a side sectional view of a valve for an internal urinary catheter according to the invention;

FIG. 4 is an exploded view of certain elements of the valve mechanism of FIG. 3;

FIG. 5 is an exploded view of an alternate embodiment of the elements of FIG. 4;

FIG. 6 is an end view of the valve mechanism of FIG. 3 in accordance with the invention;

DETAILED DESCRIPTION

Figure 7:
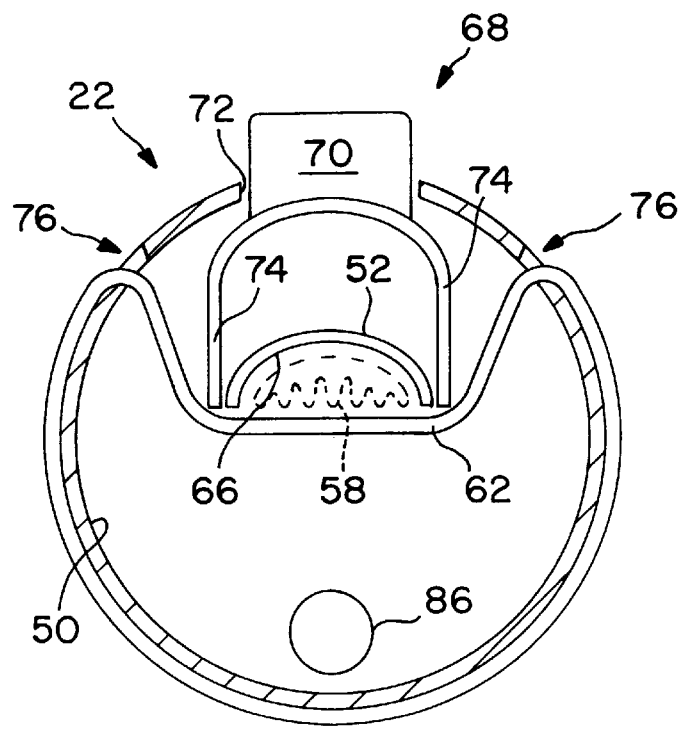
FIG. 7 is a sectional view of the valve of FIG. 3, in a compressed and closed position.

The invention relates to an internal urinary catheter, particularly a self contained internal urinary catheter for male patients particularly useful for treating obstructive uropathy or urinary incontinence. Referring to the drawings, catheter 10 in accordance with the present invention will be described.

FIG. 1 illustrates catheter 10 which includes a urine tube or cannula 12 having an inlet end 14, a urine inlet 16 at inlet end 14, an outlet end 18, a urine outlet 20 at outlet end 18, a valve mechanism 22 positioned along tube 12 for controlling flow from urine inlet 16 to urine outlet 20, a bladder retention balloon 24 positioned at inlet end 14, a urethra retention balloon 26 positioned generally at inlet end 14, and spaced toward outlet end 18 from bladder retention balloon 24, and a fluid passage 28 extending from outlet end 18 along tube 12 into communication with bladder retention balloon 24 and urethra retention balloon 26.

Urine tube 12 in accordance with the invention is preferably a generally flexible tube member made of suitable material and sized for positioning within the urethra of a patient to be treated with catheter 10 according to the invention. Urine inlet 16 at inlet end 14 of tube 12 may suitably be a number of ports or other structures suitable for allowing the inward flow of urine to be removed from the bladder. Outlet end 18 of tube 12 is preferably adapted to couple with an insertion/removal member 30 (FIG. 2) which will be described below. Tube 12 in accordance with the invention preferably has a substantially uniform shape and diameter along its length.

Valve mechanism 22 in accordance with the invention advantageously provides simple and reliable control of flow through urine tube 12. The specific details and operation of valve mechanism 22 in accordance with the invention will be described in further detail hereinbelow.

Bladder retention balloon 24 and urethra retention balloon 26 in accordance with the invention advantageously provide retention of catheter 10 in position as desired. When catheter 10 is inserted in the urethra of a patient, bladder retention balloon 24 maintains urine inlet 16 within the bladder (generally indicated at 32), and urethra retention balloon 26 prevents back migration of catheter 10 into bladder 32. As shown schematically in FIG. 1, bladder retention balloon 24 and urethra retention balloon 26 in accordance with the invention are preferably positioned for use with bladder retention balloon 24 to the bladder 32 side of the neck and orifice of bladder 32, and with urethra retention balloon 26 to the urethra side (generally indicated at 34) of the neck and orifice of bladder 32. In this manner, and advantageously, catheter 10 is securely retained in the proper position, and a seal is maintained between catheter 10 and the neck and orifice of bladder 32 so as to prevent flow of urine around the outside of catheter 10.

Referring now to FIG. 2, insertion/removal member 30 preferably includes an elongate and preferably flexible tube 36 preferably of substantially the same outside diameter as catheter 10. Tube 36 preferably has a coupling end 38 including a sleeve 40 for frictional engagement with outlet end 18 of catheter 10. Insertion/removal member 30 preferably includes a passage 42 in fluid communication with a source for providing and withdrawing balloon inflation fluid, which channel 42 may for example be connected to such a source through channel inlet port 44. Coupling end 38 preferably also includes a hollow needle member 46 in fluid communication with channel 42 for establishing inflation fluid communication with fluid passage 28 of catheter 10 as will be further discussed below.

Referring back to FIG. 1, valve mechanism 22 of the illustrated embodiment of the present invention is positioned directly at outlet end 18 of catheter 10. In this embodiment, valve mechanism 22 includes urine outlet 20 which also serves as the member for coupling with coupling end 38 of insertion/removal member 30. FIGS. 3–6 to be discussed below describe features of valve mechanism 22. It should of course be noted that urine outlet 20 and its associated elements could be provided at outlet end 18 of catheter 10, with valve mechanism 22 provided separately and, optionally, spaced from outlet end 18 of catheter 10 if desired.

Referring now to FIG. 3, valve mechanism 22 preferably includes a housing 50 preferably having substantially the same outside diameter as urine tube 12. A valve passage or sleeve 52 may suitably be provided within housing 50, for example supported by annular collars 54, 56. In further accordance with the invention, valve 22 further includes a compressible tube 58 disposed within valve passage 52 and arranged for sealing connection with a urine flow passage 60 (FIG. 1) of urine tube 12.

In accordance with the invention, a compression member 62 such as an elastic band as illustrated in FIG. 3 is positioned relative to housing 50 so as to move or compress compressible tube 58 and thereby block flow through compressible tube 58 so as to close valve 22. As shown in FIG. 3, valve passage 52 preferably has a cutout portion 64 defining a backing member 66 positioned substantially adjacent to compressible tube 58 as shown. Elastic member 62 in accordance with the invention is preferably positioned within cutout portion 64 and stretched or biased toward backing member 66 with compressible tube 58 therebetween so as to compress compressible tube 58 as desired. Still referring to FIG. 3, a push member 68 is preferably provided, movably or slidably positioned relative to housing 50, and positioned substantially adjacent to or contacting elastic member 62, most preferably in close proximity to backing member 66. In accordance with the invention, push member 68 is movable relative to housing 50 and backing member 66 between a released position illustrated in FIG. 3 wherein elastic member 62 is in a relatively relaxed state and compresses compressible tube 58 and blocks flow through valve 22, and a biased position wherein push member 68 deflects or stretches elastic member 62 away from backing member 66 into a relatively stretched state so as to at least partially release compression of compressible tube 58 and thereby allow flow through compressible tube 58 and, thereby, valve 22. Push member 68 is preferably movable relative to housing 50 of valve 22 in a direction substantially perpendicular to the flow passage of valve 22 so that application of a radially inwardly directed force serves to move push member 68 as desired. The function of push member 68, elastic member 62 and compressible tube 58 will be further described below in connection with FIGS. 7 and 8.

Referring to FIG. 4, an exploded view of push member 68, valve passage 52, compressible tube 58 and elastic member 62 is provided. Push member 68 preferably comprises a member 70 which is slidably positioned in a port 72 (FIG. 3) of housing 50 and which is arranged so as preferably to extend radially outwardly from housing 50. Push member 68 preferably further includes arm members 74 extending from member 70 to interact with elastic member 62, for deflecting elastic member 62 away from compressible tube 58 to at least partially release compression of tube 58 when desired. As shown, arm members 74 may preferably extend away from member 70 at a lateral spacing sufficient to extend to either side of backing member 66 of flow passage 60.

Elastic member 62 is preferably positioned relative to flow passage 60 so as to be positioned across backing member 66. In FIG. 4, elastic member 62 is shown in a shape induced by a combination of housing 50 and backing member 66 as will be further described.

Figure 8:
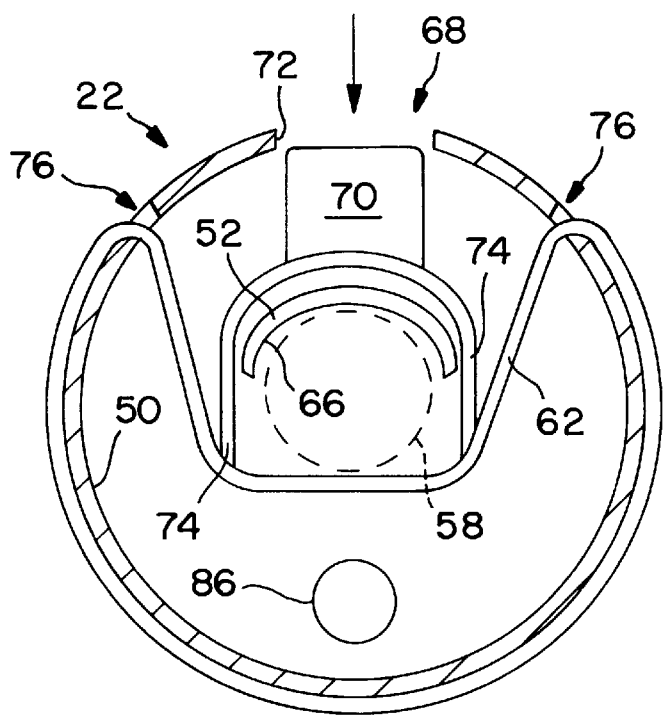
FIG. 8 is a sectional view similar to FIG. 7, with the valve in an open or released position.
Figure 9A:
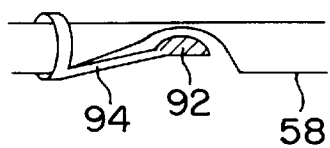
FIGS. 9a and 9b, 10a and 10b, 11a and 11b, and 12a and 12b illustrate alternative embodiments of elements of the valve member according to the invention.
Figure 9B:
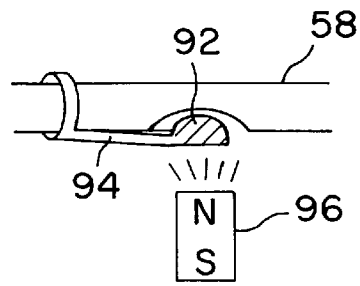

Referring to FIGS. 7 and 8, the position and operation of push member 68, flow passage 52, compressible tube 58 and elastic member 62 is readily apparent. FIG. 7 shows housing 50 having gaps 76 through which elastic member 62 is positioned. Elastic member 62 in accordance with the invention is preferably stretched around housing 50, through gaps 76, and across backing member 66 with compressible tube 58 positioned therebetween. As shown, push member 68 is preferably slidably positioned relative to housing 50 and backing member 66 with arm members 74 preferably contacting or in close association with elastic member 62 to each side of backing member 66. In this manner, radially inward movement or deflection of push member 68 as shown in FIG. 8 serves to stretch elastic member 62 and deflect same away from backing member 66, releasing compression of compressible tube 58 and thereby allowing flow therethrough.

With reference to FIGS. 3, 7 and 8, it should be readily apparent that flow through valve 22 is accomplished while isolating the various components of valve 22 from contact with urine, thereby greatly reducing the chance for bacterial colonization of catheter 10 in accordance with the invention. Specifically, compressible tube 58 carries urine flow from an inlet end 78 of valve 22 to an outlet end 80 of valve 22 without contact of urine with, for example, push member 68, elastic member 62, backing member 66 and the like.

Returning to FIG. 3, valve 22 preferably further includes a tubular portion 82 which may be a separate element or an extension of housing 50, which extends beyond collar 56 so as to define an annular space or chamber 84 between tubular portion 82 and valve passage 52. Valve 22 preferably further includes a balloon inflation fluid passage 86 which communicates with space 84 and extends from valve 22 into fluid communication with fluid passage 28. Passage 86 may suitably comprise a hollow needle member or the like preferably supported in apertures positioned in annular collars 54, 56 for stability. At outlet end 80 of valve 22, and corresponding to outlet end 18 of catheter 10, a self-sealing diaphragm 88 is preferably positioned so as to seal annular space 84. Diaphragm 88 is preferably a ring-shaped member sized to provided sealing contact with valve passage 52 and tubular portion 82. Diaphragm 88 advantageously allows piercing by hollow needle member 46 so as to allow fluid communication between annular space 84 and channel 42 of insertion/removal member 30. Further, self-sealing diaphragm 88 advantageously seals after removal of hollow needle member 46, thereby sealing balloon inflation fluid within bladder retention balloon 24 and urethra retention balloon 26 as desired. This is advantageous in accordance with the invention as the disclosed structure allows balloons 24, 26 to be inflated while catheter 10 is in position for use, entirely within the urethra.

In further accordance with the invention, and as further illustrated by the end view of FIG. 6, the provision of annular space 84 and self-sealing diaphragm 88 makes reconnection of coupling end 38 of insertion/removal member 30 with outlet end 18 of catheter 10 more readily accomplished. Specifically, coupling end 38 with hollow needle member 46 can be re-coupled with outlet end 18 of catheter 10, which corresponds in this embodiment with outlet end 80 of valve 22, regardless of the radial orientation of needle member 46 with respect to diaphragm 88 or passage 86. Referring specifically to FIG. 6, re-connection of hollow needle member 46 with passage 86 may be accomplished by piercing diaphragm 88 with hollow needle member 46 at any position in diaphragm 88, and, advantageously, not necessarily in a position aligned with passage 86.

FIGS. 7 and 8 show backing member 66 of flow passage 60 having a semi-circular shape defining a concave contour facing compressible tube 58. In accordance with an alternative embodiment of the invention, elastic member 62 may be provided having a convex contour substantially matching the concave contour of backing member 66 so as to provide a more effective compression and blockage of flow through compressible tube 58. As shown in FIG. 5, for example, elastic member 62 may be provided with a thickened portion 90 arranged to mate with backing member 66 as desired. Of course, it should be appreciated that backing member 66 may be provided having numerous different types or shapes of contour, and that elastic member 62 according to the invention could likewise be provided with a matching contour as desired.

FIGS. 9–12 illustrate several alternative embodiments of structure for compressing compressible tube 58 as desired in accordance with the invention. Referring to FIGS. 9a–9b, a magnetic compression member 92 may be provided, and positioned at the end of an elastic arm 94 substantially rigidly mounted, for example, to flow passage 60 or any other substantially rigid structure of valve 22. Arm 94 in accordance with this embodiment is preferably biased to an inwardly directed position as shown in FIG. 9a, wherein compression member 92 cooperates with a backing member (not shown) to compress compressible tube 58 as desired. In accordance with this embodiment, positioning of a magnetic releasing member 96 (FIG. 9b) within sufficiently close proximity to magnetic compression member 92 results in attraction of compression member 92 toward magnetic releasing member 96 so as to deflect arm 94 and, thereby, magnetic compression member 92 away from the backing member, thereby at least partially releasing compression and blocking of compressible tube 58.

Figure 10A:
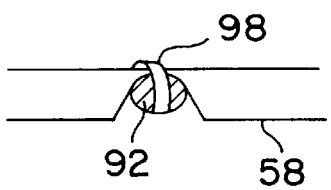
Figure 10B:
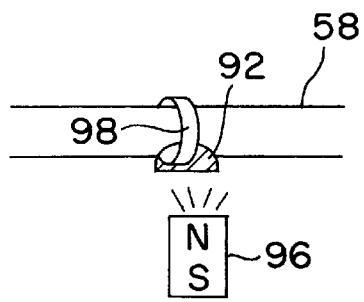

FIGS. 10a–10b illustrate a similar alternative embodiment wherein magnetic compression member 92 is elastically held with reference to the backing member (not shown) by an elastic band member 98 positioned around the backing member, compressible tube 58 and magnetic compression member 92. In a similar manner to the embodiment of FIGS. 9a–9b, positioning of a magnetic release member 96 in sufficiently close proximity results in an attraction of magnetic compression member 92 toward magnetic release member 96 as shown, thereby stretching elastic band member 98 and at least partially releasing compression of compressible tube 58.

Figure 11A:
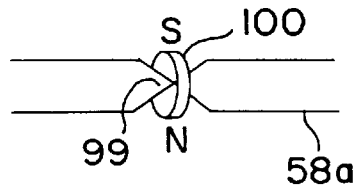
Figure 11B:
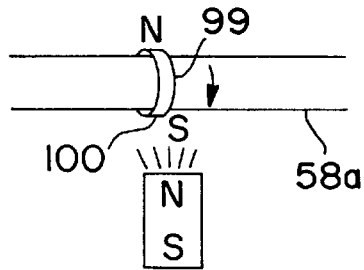

Referring to FIGS. 11a–11b, a still further alternative embodiment of the invention with respect to the compression and releasing of compression of compressible tube 58 is illustrated. As shown, compressible tube 58a may be provided having a section 99 biased toward a twisted and, thereby, compressed and closed position. A polar magnetic member 100 may suitably be provided, preferably mounted in close proximity to section 99 and having north and south poles as illustrated in the drawing, whereby positioning of magnetic release member 96 as shown in FIG. 11b attracts north pole of magnetic member 100 thereby twisting compressed section 99 to a straightened position as shown in FIG. 11b, wherein compression of compressible tube 58a is released, and flow is allowed.

Figure 12A:
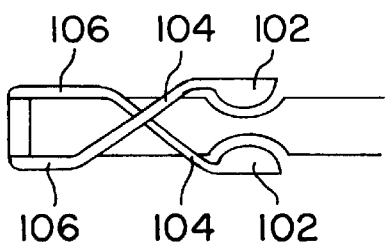
Figure 12B:
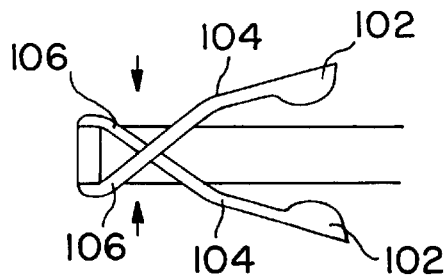

FIGS. 12a–12b illustrate still another alternative embodiment of the invention drawn to an alternative structure for compressing compressible tube 58. In accordance with the embodiment of FIGS. 12a–12b, two compression members 102 are provided, preferably positioned at the ends of flexible arms 104. As shown in FIG. 12a, arms 104 may be spiralled a half rotation with respect to compressible tube 58 so as to arrange compressible members 102 in a position whereby a compressive force directed at base portions 106 of arms 104 results in a spreading of compression members 102 as shown in FIG. 12b.

With reference to the above described various embodiments of the present invention for applying and releasing compression to and from compressible tube 58, it should be readily apparent that each embodiment allows for reliable and simple compression of tube 58 to provide effective blockage of flow through valve 22. Further, release of compression of tube 58 is accomplished in each embodiment through the simple positioning of a magnetic release member, or through the application of a simple radially inwardly directed compressive force which is both dictated by the anatomy in which catheter 10 is positioned and used and readily accomplished with catheter 10 of the present invention.

Figure 13:
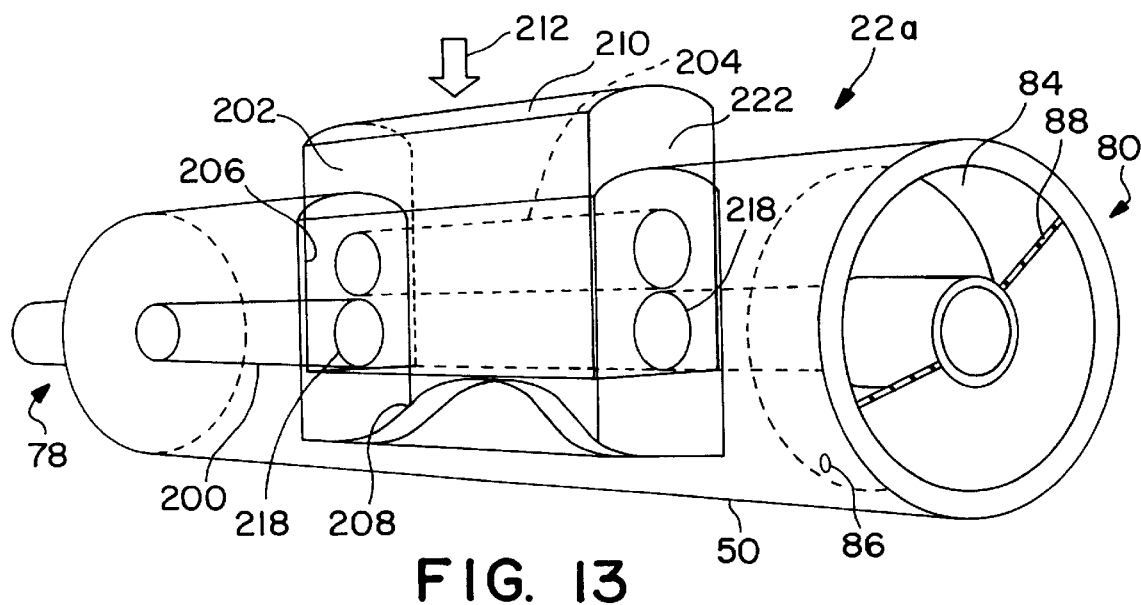
FIG. 13 illustrates an alternative embodiment of a valve member according to the invention.
Figure 14:
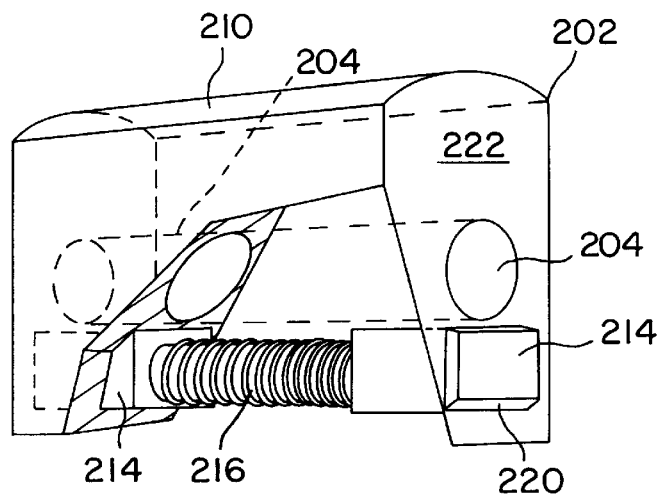
FIG. 14 illustrates a further alternative embodiment similar to FIG. 13.

Referring now to FIGS. 13 and 14, an alternative embodiment of valve 22a is shown wherein housing 50 defines a valve passage 200 for positioning along a urine tube or passage of a catheter as discussed above. Valve 22a further includes a valve passage member 202 which is moveably positioned relative to housing 50, and which defines a portion 204 of valve passage 200 which is moveable relative to valve passage 200 between a substantially blocked position as illustrated in FIG. 13, and a flow position which will be discussed below. In accordance with this embodiment of the invention, housing 50 has a well 206 for receiving valve passage member 202, and preferably further includes a biasing element such as spring 208 for biasing valve passage member 202 toward the position illustrated in FIG. 13 wherein portion 204 is laterally positioned away from the remainder of valve passage 200 so as to substantially block flow through valve 22a. From the blocked position of FIG. 13, application of force to a force receiving portion 210 of valve passage member 202 as shown by arrow 212 serves to overcome spring 208 and thereby laterally move valve passage member 202 so as to align portion 204 with valve passage 200 and allow flow through same.

It should be noted that valve 22, 22a preferably includes a latex rubber sheath or the like for enclosing the entire structure thereof, and that in the embodiment illustrated in FIG. 13, this sheath (not shown) serves to hold valve passage member 202 within well 206 as desired.

Referring now to FIG. 14, an alternative embodiment of valve passage member 202 is provided wherein sealing members or inserts 214 are provided, longitudinally moveable with respect to portion 204, and biased outwardly away from each other for example by spring 216 so as to substantially sealingly engage with inner end portions 218 of valve passage 200 when valve passage member 202 is in the blocked position as shown in FIG. 13. Inserts 214 are preferably provided in size and shape to enhance the sealing engagement of inserts 214 with inner end portions 218 as desired. In this regard, inserts 214 may be provided with a lower slopped portion 220 or similar structure, for facilitating withdrawal of inserts 214 into valve passage member 202 and against the bias of spring 216 upon the application of downward force as shown by arrow 212 on valve passage member 202. In this manner, advantageously, inserts 214 sealably engage end portions 218 of valve passage 200 in the blocked position, and readily withdraw into valve passage member 202 when desired to allow positioning of valve passage member 202 with portion 204 in the flow position.

Further alternatively, side portions 222 of valve passage member 202 may be readily adapted for sealable and slidable interaction with inner walls of well 206 so as to provide the desired movement of valve passage member 202 while substantially preventing flow or leakage through or around valve passage member 202 when valve passage member 202 is in the blocked position.

As with the above described embodiments of valve 22, it should be noted that valve 22a in accordance with this alternative embodiment advantageously allows valve 22a to be controlled through application of a lateral force in the direction of arrow 212, which can readily be accomplished, advantageously, with catheter 10 including valve 22a positioned as an indwelling unit.

In accordance with the invention, a catheter 10 is positioned for use as follows.

Initially, catheter 10 is coupled with insertion/removal member 30 by connecting coupling end 38 to outlet end 80 of valve 22. In this connected position, sleeve 40 is positioned over outlet end 80, and hollow needle member 46 pierces diaphragm 88 so that fluid passage 28 and, thereby, balloons 24, 26 are in fluid communication with hollow needle 46 and, thereby, a source of balloon inflation fluid. The assembly is then inserted into the urethra with inlet end 16 of catheter being inserted first. Catheter 10 is inserted until urine inlet 16 is positioned within bladder 32 as shown schematically in FIG. 1, with bladder retention balloon 24 positioned within bladder 32 and urethra retention balloon 26 positioned just inside urethra 34 as schematically shown in FIG. 1. At this point, balloon inflation fluid is introduced through channel 42, through hollow needle member 46 into annular space 84, and into fluid passage 28, eventually reaching balloons 24, 26 so as to inflate same to the desired size. In this regard, bladder retention balloon 24 is preferably provided from a material which will allow a relatively greater expansion than urethra retention balloon 26 in response to the same pressure of inflation fluid. For example, with catheter 10 having a size of approximately 16 French, urethra retention balloon 26 may be expandable, for example, to about 22 French, while bladder retention balloon is expandable to a somewhat larger size.

Upon proper inflation of balloons 24, 26, catheter 10 is properly retained with respect to bladder 32 and urethra 34, and is thereby held properly within bladder 32 against back migration of the entire device into bladder 32. At this point, insertion/removal member 30 is released from connection with catheter 10, and hollow needle member 46 is withdrawn from self-sealing diaphragm 88, which seals upon such removal and thereby seals balloon inflation fluid within balloons 24, 26 as desired. Insertion/removal member 30 is then removed from the urethra, and catheter 10 is properly inserted for use.

Valve 22 in accordance with the invention can then be operated, depending upon the embodiment in use, through application of compressive force or proper positioning of a magnetic means, so as to release compression of compressible tube 58 within valve 22, and thereby allow flow of urine from bladder 32, into urine inlet 16, through urine tube 12 and valve 22 to urine outlet 20 as desired.

It should be appreciated that catheter 10 in accordance with the invention is designed so as to provide a relatively long-term correction to the above-noted uropathy and incontinence problems. In this regard, a membrane or other member may suitably be positioned over valve 22, for example as shown in FIG. 1. This is advantageous so as to limit the exposure of various components of valve 22 to contact with urethra 34 as well.

It should also be appreciated that, because catheter 10 is designed as an indwelling member having minimal parts exposed to urine flow, the colonization of bacteria and other causes of infection are significantly impeded or removed.

If it is desired to remove catheter 10 after installation, insertion/removal member 30 is re-inserted into urethra 34 so as to connect coupling end 38 with outlet end 80, and reintroduce hollow needle member 46 through diaphragm 88 into annular space 84. Once this connection is completed, balloon inflation fluid can be removed from balloons 24, 26 so as to deflate same, and coupled catheter 10 and insertion/removal member 30 can be removed from bladder 32 and urethra 34 as desired.

Figure 15A:
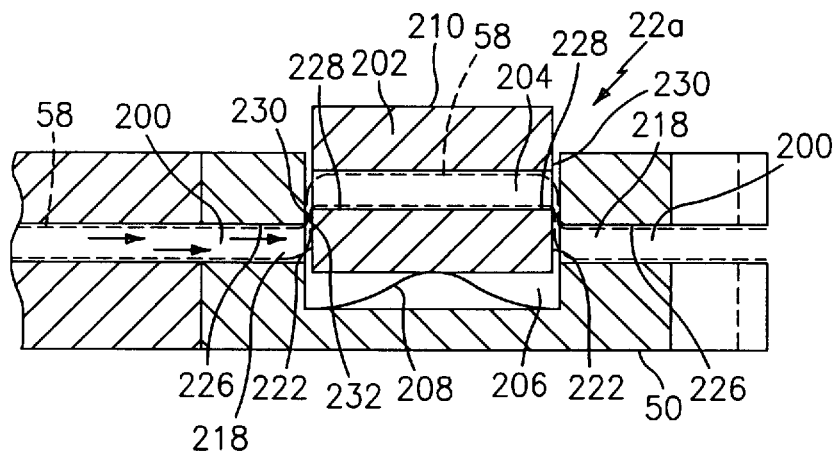
FIGS. 15a, 15b and 15c illustrate an alternative method of use of the present invention.
Figure 15B:
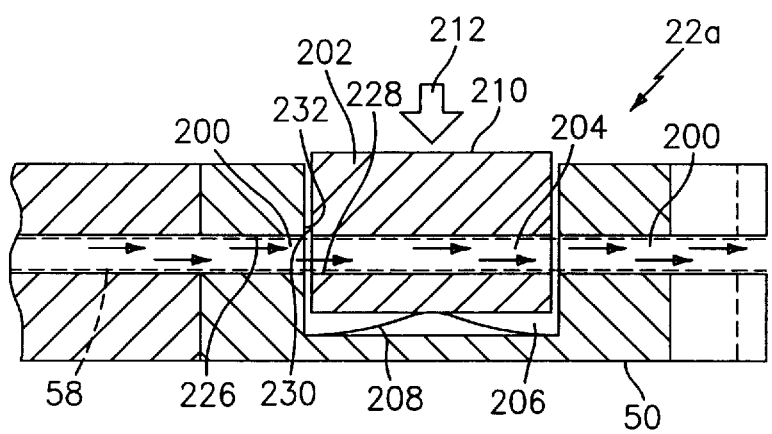
Figure 15C:
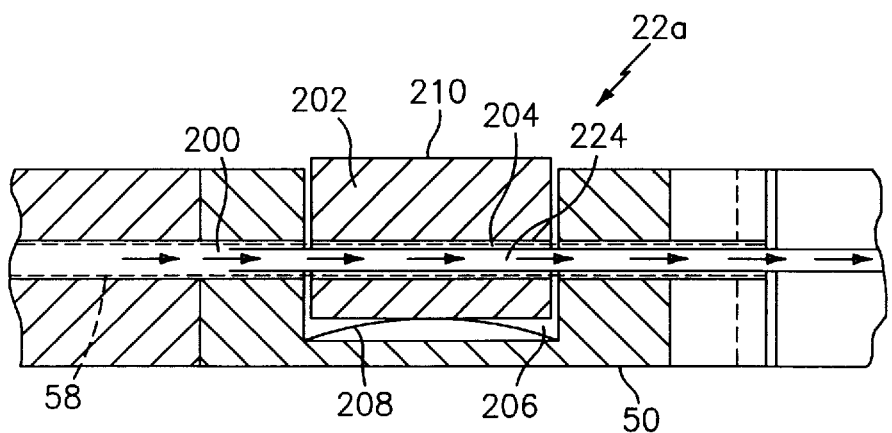

Referring to FIGS. 15a, 15b and 15c, a method of operation of the alternative embodiment of FIGS. 13 and 14 will be described.

FIGS. 15a–15c further illustrate an alternative embodiment of the present invention wherein valve 22a includes a tube 58 which is disposed through valve passage 200 including portion 204.

As shown in FIG. 15a, valve 22a is provided with valve passage member 202 biased toward the blocked position illustrated so as to substantially block or prevent flow through portion 204 or valve 22a in general. When it is desired to allow flow through valve 22a so as to void the bladder of a patient, force is applied laterally and inwardly directed as shown by arrow 212 so as to position valve passage member 202 against the bias of spring 208 into the flow position illustrated in FIG. 15b wherein portion 204 is at least partially aligned with valve passage 200 to allow flow therethrough. In accordance with one embodiment of this invention, valve passage member 202 can be held in the position illustrated in FIG. 15b until sufficient drainage is accomplished, at which point releasing or removing the force applied to valve passage member 202 results in spring 208 biasing valve passage member 202 back toward the position of FIG. 15a, wherein portion 204 is laterally removed from alignment with valve passage 200 and flow through valve 22a is substantially blocked.

Alternatively, and referring to FIG. 15c, a collecting member 224 may be positioned within valve 22a so as to extend at least partially into portion 204 as shown, such that releasing force in the direction of arrow 212 will nevertheless result in collecting member 224 holding valve passage member 202 in the flow position illustrated. In this configuration, valve 22a can readily be used as a more conventional Foley catheter, for example in connection with treatment of custodial patients. In this regard, the structure of valve 22a is particularly advantageous in that removal of collecting member 224, either intentionally or otherwise, results in valve passage member 202 being released such that spring 208 positions valve passage member 202 laterally outwardly toward the position of FIG. 15a, thereby removing portion 204 from alignment with valve passage 200 and blocking flow through valve 22a as desired.

In the embodiment of valve 22a including tube 58, positioning valve passage member 202 in the blocking position of FIG. 15a serves to pinch off tube 58 between edges 226, 228 and/or facing surfaces 230, 232 of valve passage 200 and valve passage member 202.

Figure 16A:
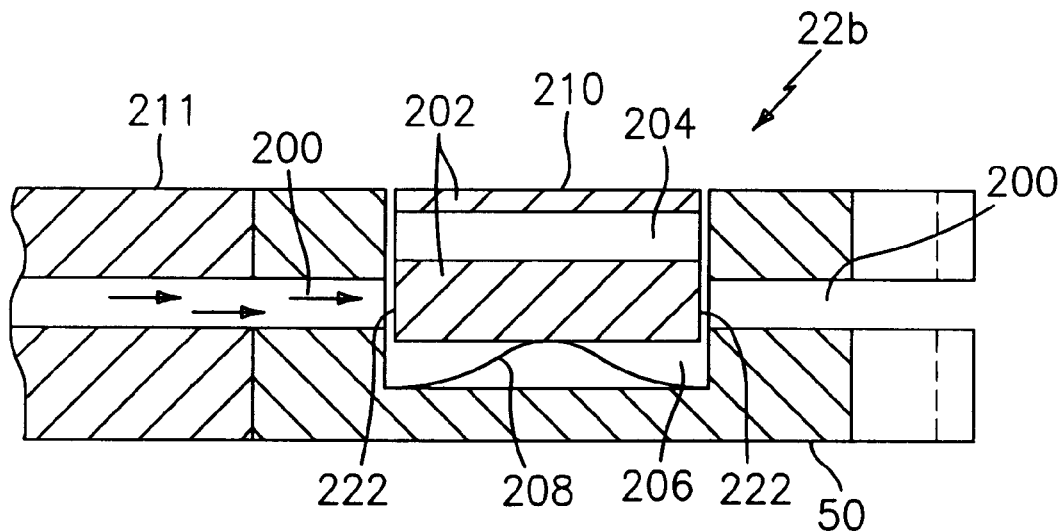
FIGS. 16a and 16b illustrate a further alternative embodiment of the invention.
Figure 16B:
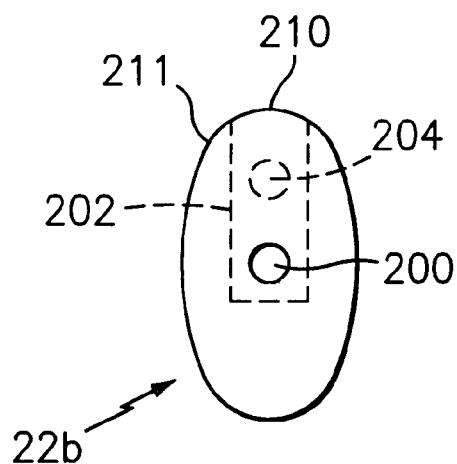

Referring now to FIGS. 16a and 16b a further alternative embodiment of a valve 22b according to the invention may be provided wherein force receiving portion 210 of valve passage member 202 is positioned flush with the outside surface 211 of the remainder of valve 22b. This advantageously serves to avoid any extension or bulges around the perimeter of valve 22b. It may also be advantageous in this embodiment to provide valve 22b and/or cannula 12 having an oval or other smooth non-round shape (FIG. 16b) which serves to resist rotating of the device within the urethra of a patient. In this way, the device of the present invention could be implanted having force receiving portion 210 arranged in a known direction for actuation as needed. Of course, this configuration could be utilized in the other embodiments of the present invention as well.

In accordance with the foregoing, it should be readily apparent that a catheter, a valve for a catheter, and methods for using same have been disclosed in accordance with the invention so as to accomplish each and every object set forth hereinabove.

It is to be understood that the invention is not limited to the illustrations described and shown herein, which are deemed to be merely illustrative of the best modes of carrying out the invention, and which are susceptible of modification of form, size, arrangement of parts and details of operation. The invention rather is intended to encompass all such modifications which are within its spirit and scope as defined by the claims.

What is claimed is:

1. An internal urinary catheter, comprising:
   a cannula having a urine passage, a urine inlet and a urine outlet; and
   valve means positioned along said urine passage between said inlet and said outlet and comprising a valve passage having at least a portion which is moveably positioned between a substantially blocked position and a flow position, and means for moving said portion, said means for moving being biased toward a blocking position wherein said portion is in said substantially blocked position and flow through said valve means is substantially blocked, and said means for moving being moveable to a released position at least partially moving said portion toward said flow position wherein flow through said valve means is allowed, wherein said portion comprises a compressible tube, and wherein said means for moving comprises means for releasably compressing said tube in said substantially blocked position, said means for releasably compressing being positionable to said released position wherein compression of said tube is at least partially reduced.

2. A catheter according to claim 1, wherein said valve means further comprises a sleeve positioned along said cannula and having a cutout portion, said compressible tube being positioned within said sleeve, and wherein said means for releasably compressing is biased against said tube at said cutout so as to block flow through said tube.

3. A catheter according to claim 2, wherein said valve means further comprises elastic means positioned across said cutout to compress said tube, and means for pushing said elastic means away from said cutout whereby compression of said tube is at least partially released.

4. A catheter according to claim 3, wherein said means for pushing comprises a push member slidably positionable relative to said sleeve and having at least one arm member contacting said elastic means substantially adjacent to said cutout whereby sliding said push member relative to said sleeve positions said means for releasably compressing between said compressing position and said released position.

5. A catheter according to claim 4, wherein said elastic member biases said push member into said compressing position.

6. A catheter according to claim 2, wherein said sleeve has a contour at said cutout, and wherein said means for releasably compressing includes a contact portion shaped to substantially match said contour whereby blockage of flow in said compressed position is enhanced.

7. A catheter according to claim 1, further comprising retention means for retaining said inlet end of said cannula with respect to a bladder of a patient.

8. A catheter according to claim 7, wherein said retention means comprises inflatable retention means, a fluid channel disposed along said cannula and communicating with said inflatable retention means, and fluid introduction means associated with said fluid channel for introducing fluid into said fluid channel whereby said inflatable retention means can be inflated for securing said cannula in position.

9. A catheter according to claim 8, wherein said means for introducing comprises a chamber communicated with said fluid channel, and means for communicating a source of fluid with said chamber.

10. A catheter according to claim 9, wherein said means for communicating comprises a self-sealing diaphragm positioned over said chamber.

11. A catheter according to claim 10, wherein said source of fluid comprises a hollow member for puncturing said self-sealing diaphragm so as to introduce said fluid to said chamber, whereby said hollow member can be introduced at any point in said diaphragm into said chamber to communicate with said fluid channel.

12. A catheter according to claim 11, wherein said chamber comprises a tubular member positioned around said cannula so as to define an annular space wherein said fluid channel communicates with said annular space, and wherein said self-sealing diaphragm comprises a ring positioned over said cannula substantially adjacent said annular space.

13. A catheter according to claim 12, further comprising insertion means for inserting said cannula in the urethra of a patient and for inflating said inflatable retention means when said outlet end of said cannula is within the urethra.

14. A catheter according to claim 13, wherein said insertion means comprises a sleeve member and coupling means for coupling said sleeve member to said outlet end, and wherein said means for inflating comprises means associated with said coupling means for introducing fluid into said filling channel.

15. A catheter according to claim 14, wherein said means for introducing comprises hollow means for puncturing said diaphragm, said hollow means being connected to a source of fluid.

16. A catheter according to claim 8, further comprising insertion means for inserting said cannula in the urethra of a patient and for inflating said inflatable retention means when said outlet end of said cannula is within the urethra.

17. A catheter according to claim 16, wherein said insertion means comprises a sleeve member and coupling means for coupling said sleeve member to said outlet end, and wherein said means for inflating comprises means associated with said coupling means for introducing fluid into said fluid channel.

18. A catheter according to claim 7, wherein said retention means comprises a bladder retention member positioned along said cannula at said inlet end, and a urethral retention member spaced toward said outlet end from said bladder retention member.

19. A catheter according to claim 18, wherein said bladder retention member comprises a bladder retaining balloon, and said urethral retention member comprises a urethral retaining balloon, and further comprising fluid channel means disposed along said cannula and communicating with said bladder retaining balloon and said urethral retaining balloon and fluid introduction means for introducing fluid into said fluid channel means whereby said bladder retaining balloon and said urethral retaining balloon can be inflated for securing said cannula in position.

20. A catheter according to claim 19, wherein said fluid channel means comprises a fluid channel communicated with both of said bladder retaining balloon and said urethral retaining balloon.

21. A catheter according to claim 19, wherein said bladder retaining balloon and said urethral retaining balloon are provided from materials having different elasticity whereby said bladder retaining balloon inflates to a size greater than said urethral retaining balloon when subjected to fluid at the same pressure.

22. A catheter according to claim 1, wherein said cannula has an exterior diameter and said valve means has an exterior diameter substantially the same as said external diameter of said cannula.

23. A catheter according to claim 22, wherein said means for moving extends beyond said external diameter of said valve means.

24. A catheter according to claim 1, wherein said cannula and said valve means have an external surface which is substantially oval-shaped.

25. An internal urinary catheter, comprising:
a cannula having a urine passage, a urine inlet and a urine outlet; and
valve means positioned along said urine passage between said inlet and said outlet and comprising a valve passage having at least a portion which is moveably positioned between a substantially blocked position and a flow position, and means for moving said portion, said means for moving being biased toward a blocking position wherein said portion is in said substantially blocked position and flow through said valve means is substantially blocked, and said means for moving being moveable to a released position at least partially moving said portion toward said flow position wherein flow through said valve means is allowed, wherein said portion comprises a valve passage member having a valve passage defined therein, said valve passage member being movably mounted in said valve means between said blocked position wherein said valve passage is substantially isolated from said urine passage and flow through said valve means is substantially blocked, and said flow position wherein said valve passage is communicated with said urine passage and flow through said valve passage and said valve means is allowed.

26. A catheter according to claim 25, wherein said valve passage member is laterally moveable with respect to said urine passage between said blocked position and said flow position.

27. A catheter according to claim 25, wherein said means for releasably moving comprises resilient biasing means for biasing said valve passage member toward said blocked position, and push surface means associated with said valve passage member for receiving a pushing force to overcome said means for biasing and for moving said valve passage member to said flow path.

28. A catheter according to claim 25, wherein said valve passage member has side surfaces arranged to substantially block said urine passage in said blocked position.

29. A catheter according to claim 25, wherein said valve passage member further comprises seal means moveably positioned relative to said valve passage member for substantially sealably engaging said urine passage when said valve passage member is in said blocked position.

30. A catheter according to claim 29, wherein said seal means comprises insert members moveably positioned relative to said valve passage member between an extended position for sealably engaging said urine passage, and a withdrawn position allowing movement of said valve passage member to said flow position.

31. A valve for an internal urinary catheter, comprising:
a passage for urine flow;
a valve passage positioned along said passage and having at least a portion which is moveably positioned between a substantially blocked position and a flow position; and
means for moving said portion, said means for moving being biased toward a blocking position wherein said portion is in said substantially blocked position and flow through said valve passage is substantially blocked, and said means for moving being movable to a released position at least partially moving said portion toward said flow position wherein flow through said valve passage is allowed, wherein said portion comprises a compressible tube, and wherein said means for moving comprises means for releasably compressing said tube in said substantially blocked position, said means for releasably compressing being positionable to said released position wherein compression of said tube is at least partially released.

32. A valve according to claim 31, wherein said tube is sealingly associated with said passage, whereby said means for releasably compressing is isolated from flow through said passage and said tube.

33. A valve according to claim 32, further comprising an inflation fluid channel positioned substantially adjacent to said passage.

34. A valve according to claim 33, wherein said passage has an inlet end and an outlet end, and further comprising:
a tubular member positioned around said outlet end so as to define an annular space therebetween, said annular space having an outlet end and said channel being in fluid communication with said annular space; and
self-sealing diaphragm means positioned within said outlet end of said annular space whereby communication can be established with said channel through any point of said diaphragm.

35. A valve according to claim 31, wherein said means for releasably compressing comprises a backing member positioned substantially adjacent to said tube, and a compression member movably positioned relative to said backing member between a compressing position wherein said compression member compresses said tube against said backing member, and a released position wherein said compression member is positioned away from said backing member so as to allow flow through said tube.

36. A valve according to claim 35, wherein said tube has a longitudinal axis, and wherein said compression member is movable relative to said backing member in a direction substantially perpendicular to said longitudinal axis.

37. A valve according to claim 35, wherein said backing member comprises a sleeve having a cutout, said tube being positioned within said sleeve and traversing said cutout, and said compression member being movably positioned within said cutout relative to said backing member.

38. A valve according to claim 35, wherein said backing member has a contour facing said tube and said compression member has a compression contour facing and substantially matching said contour of said backing member whereby blockage of flow in said compressing position is facilitated.

39. A valve according to claim 35, wherein said compression member is an elastic member disposed across said backing member and compressing said tube against said backing member in a relatively relaxed state so as to block flow through said tube, and further comprising means for deflecting said elastic means away from said backing member into a relatively stretched state so as to allow flow through said tube, said elastic member being biased toward said relatively relaxed state.

40. A valve according to claim 39, wherein said means for deflecting comprises a push member movably positioned relative to said backing member and contacting said elastic member, said push member being movable between a deflecting position wherein said elastic member is deflected to said stretched state, and a released position wherein said elastic member returns to said relaxed state.

41. A valve according to claim 40, further comprising a housing positioned around said tube, said push member being slidably mounted in said housing and having a radially outwardly projecting portion whereby said push member can be operated by force applied exterior of said housing.

42. A valve according to claim 35, wherein said compression member comprises a magnetic compression member elastically biased against said backing member into said compressing position, and magnetic means for attracting said magnetic member, whereby positioning said magnetic means substantially adjacent to said magnetic compression member moves said compression member to said released position.

43. A valve according to claim 31, wherein said means for releasably compressing comprises two compression members each elastically mounted substantially adjacent to said tube having a bias toward a compressing position wherein said two compression members compress said tube therebetween, and wherein said two compression members are movable against said bias to a released position wherein said two compression members are spread relative to said compressing position.

44. A valve for an internal urinary catheter, comprising:

a passage for urine flow;

a valve passage positioned along said passage and having at least a portion which is moveably positioned between a substantially blocked position and a flow position; and means for moving said portion, said means for moving being biased toward a blocking position wherein said portion is in said substantially blocked position and flow through said valve passage is substantially blocked, and said means for moving being movable to a released position at least partially moving said portion toward said flow position wherein flow through said valve passage is allowed, wherein said portion comprises a valve passage member having a valve passage defined therein, said valve passage member being movably mounted in said valve means between said blocked position wherein said valve passage is substantially isolated from said urine passage and flow through said valve means is substantially blocked, and said flow position wherein said valve passage is communicated with said urine passage and flow through said valve passage and said valve means is allowed.

45. A valve according to claim 44, wherein said valve passage member is laterally moveable with respect to said urine passage between said blocked position and said flow position.

46. A catheter according to claim 44, wherein said means for releasably moving comprises resilient biasing means for biasing said valve passage member toward said blocked position, and push surface means associated with said valve passage member for receiving a pushing force to overcome said means for biasing and for moving said valve passage member to said flow path.

47. A catheter according to claim 44, wherein said valve passage member has side surfaces arranged to substantially block said urine passage in said blocked position.

48. A catheter according to claim 44, wherein said valve passage member further comprises seal means moveably positioned relative to said valve passage member for substantially sealably engaging said urine passage when said valve passage member is in said blocked position.

49. A catheter according to claim 48, wherein said seal means comprises insert members moveably positioned relative to said valve passage member between an extended position for sealably engaging said urine passage, and a withdrawn position allowing movement of said valve passage member to said flow position.

50. A method of controlling urine flow in the urethra, comprising the steps of:

providing a cannula having a urine passage, an inlet end having a urine inlet, an outlet end having a urine outlet and valve means positioned along said urine passage for limiting flow from said urine inlet to said urine outlet, said valve means comprising a valve passage having at least a portion which is moveably positioned between a substantially blocked position and a flow position, and means for moving said portion, said means for moving being biased toward a blocking position wherein said portion is in said substantially blocked position and flow through said valve means is substantially blocked, and said means for moving being moveable to a released position at least partially moving said portion toward said flow position wherein flow through said valve means is allowed;

positioning said cannula in the urethra with said urine inlet in the bladder; and moving said means for moving to said released position so as to allow flow of urine from the bladder through said urine passage and said valve passage to said urine outlet, wherein said portion comprises a compressible tube, and wherein said means for moving comprises means for releasably compressing said tube in said substantially blocked position, said means for releasably compressing being positionable to said released position wherein compression of said tube is at least partially released, whereby said means for releasably compressing is isolated from urine flow through said valve means.

51. A method according to claim 49, wherein said valve means comprises a movable compression member movable between said substantially blocked position and said released position in a direction substantially perpendicular to a longitudinal axis of said compressible tube, and wherein said step of moving said means for releasably compressing comprises the step of applying a compressive force to said means for releasably compressing so as to move said compression member to said released position.

52. A method according to claim 51, further comprising the step of releasing said compressive force whereby said compression member returns to said compressing position to block flow of urine through said valve.

53. A method according to claim 52, wherein said step of positioning said urine cannula further comprises positioning said urine cannula in the urethra with said urine outlet and said valve within the urethra, and wherein the step of applying said compressive force comprises applying said force external of said urethra.

54. A method according to claim 49, further comprising the step of positioning a substantially tubular collecting member within said valve means and extending at least partially into said portion with said portion in said flow position so that said collecting member holds said portion in said flow position.

55. A method according to claim 49, wherein said portion comprises a valve passage member having a valve passage defined therein, said valve passage member being movably mounted in said valve means between said blocked position wherein said valve passage is substantially isolated from said urine passage and flow through said valve means is substantially blocked, and said flow position wherein said valve passage is communicated with said urine passage and flow through said valve passage and said valve means is allowed.

* * * * *